(12) United States Patent
Weis et al.

(10) Patent No.: US 8,455,700 B2
(45) Date of Patent: Jun. 4, 2013

(54) METHOD FOR PRODUCING PHENYLALKANE-1-OLS

(75) Inventors: Martine Weis, Mannheim (DE); Daniel Breuninger, Bobenheim-Roxheim (DE); Klaus Ebel, Lampertheim (DE); Harald Winsel, Freinsheim (DE)

(73) Assignee: BASF SE, Ludwigshafen (DE)

( * ) Notice: Subject to any disclaimer, the term of this patent is extended or adjusted under 35 U.S.C. 154(b) by 267 days.

(21) Appl. No.: 13/054,108

(22) PCT Filed: Jul. 27, 2009

(86) PCT No.: PCT/EP2009/059638
§ 371 (c)(1),
(2), (4) Date: Jan. 14, 2011

(87) PCT Pub. No.: WO2010/012675
PCT Pub. Date: Feb. 4, 2010

(65) Prior Publication Data
US 2011/0118510 A1 May 19, 2011

(30) Foreign Application Priority Data
Aug. 1, 2008 (EP) .................................... 08161643

(51) Int. Cl.
*C07C 29/149* (2006.01)

(52) U.S. Cl.
USPC ........................................................ 568/814

(58) Field of Classification Search
USPC ........................................................ 568/814
See application file for complete search history.

(56) References Cited

FOREIGN PATENT DOCUMENTS

| DE | 40 747 | 8/1887 |
| WO | 2006 125026 | 11/2006 |

OTHER PUBLICATIONS

Kazuyuki Hattori, et al., "Chemoselective Control of Hydrogenation Among Aromatic Carbonyl and Benzyl Alcohol Derivatives using Pd/C(en) Catalyst", Tetrahedron, 57, 2001, pp. 4817-4824.
Augustine Silveira, Jr., et al., "A Synthesis of 2,3-Dihydro-1H-Cyclopenta[α]chrysene", J. Org. Chem., vol. 37, No. 23, 1972, pp. 3687-3691.
Karl Kindler, et al., "Über Neue und über Verbesserte Wege zum Aufbau von Pharmakologisch Wichtigen Karbonsäuren. I." Arch. Pharm., 1933, 271, pp. 431-439.
Neal J. Green, et al., "Structure-Activity Studies of a Series of Dipyrazolo[3,4-b:3',4'-d]pyridin-3-ones Binding to the Immune Regulatory Protein B7.1", Bioorganic & Medicinal Chemistry, 11(13), 2003, pp. 2991-3013.
Gregory S. Hamilton, et al., "Synthesis of N-Glyoxyl Prolyl and Pipecolyl Amides and Thioesters and Evaluation of Their in Vitro and in Vivo Nerve Regenerative Effects", J. Med. Chem., 45, (16), 2002, pp. 3549-3557.
Xin Wang, et al., "Synthesis of Cinacalcet Congeners", Tetrahedron Letters, 45, 2004, pp. 8355-8358.
International Search Report issued Sep. 22, 2009 in PCT/EP09/59638 filed Jul. 27, 2009.
Saudan, A. Lionel et al., "Dihydrogen Reduction of Carboxylic Esters to Alcohols under the Catalysis of Homogeneous Ruthenium Complexes: High Efficiency and Unprecedented Chemoselectivity", Angewandte Chemie, vol. 119, pp. 7617-7620, XP002545260, (2007).

*Primary Examiner* — Brian J Davis
(74) *Attorney, Agent, or Firm* — Oblon, Spivak, McClelland, Maier & Neustadt, L.L.P.

(57) ABSTRACT

The present invention relates to a process for preparing phenylalkan-1-ols in three stages, where an ester condensation in the presence of alkali metal or alkaline earth metal alcoholates is carried out in the first stage.

10 Claims, No Drawings

METHOD FOR PRODUCING PHENYLALKANE-1-OLS

The present invention relates to a process for preparing phenylalkan-1-ols in three stages, where an ester condensation in the presence of alkali metal or alkaline earth metal alcoholates is carried out in the first stage.

There is a great need for phenylalkan-1-ols which are used as precursor or intermediate for a wide variety of applications such as, inter alia, fragrances, active pharmaceutical ingredients or crop protection agents. Thus, for example, 3-(3'-trifluoromethylphenyl)propan-1-ol (3-TFMPP) is a possible precursor in the synthesis of the pharmaceutical cinacalcet (Mimpara®, Sensipar®) which is employed in the therapy of secondary hyperparathyroidism.

WO 2006125026 describes various routes to cinacalcet starting from 3-(3'-trifluoro-methylphenyl)propylamine, 3-(3'-trifluoromethylphenyl)propionaldehyde, 3-(3'-trifluoromethylphenyl)propionitrile and 3-(3'-trifluoromethylphenyl)propan-1-ol (3-TFMPP). The synthesis of cinacalcet starting from 3-TFMPP includes the conversion of the OH group into a good leaving group and followed by reaction with (R)-naphthylethylamine in the presence of a base. This route has several advantages over other synthetic routes. Thus, for example, the use of substances which are toxic, costly and difficult to handle, such as Ti(Oi—Pr)$_4$, NaBH$_3$CN, oxalyl chloride or dimethyl sulfoxide is avoided.

In this connection, WO 2006125026 describes two different possibilities for synthesizing the alcohol, both of which start from 1-bromo-3-(trifluoromethyl)benzene. The aromatic compound is subjected to a Heck cross-coupling with acrolein dialkyl acetal or acrylic ester and then reduced to the alcohol. It is possible in this case for double bond and carbonyl group to be reduced in any sequence. In the examples, metal hydrides are indicated for the reduction of the carbonyl group and a hydrogenation of the double bond with hydrogen in the presence of Pd/C as catalyst is indicated as preferred. Disadvantages of this procedure compared with the process disclosed herein are the use of costly Pd catalysts for the Heck coupling, and the use of metal hydrides, which are problematic in terms of safety, for reducing the carbonyl group.

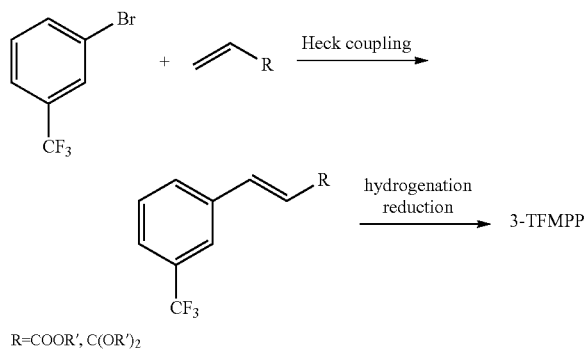

R=COOR', C(OR')$_2$

X. Wang et al. describe in a brief footnote in Tetrahedron Letters 2004, 45, 8355-8358 another possible route to 3-TFMPP by hydrogenation of the corresponding CF$_3$-substituted cinnamic acid and subsequent reduction of the acid to the alcohol with LiAlH$_4$.

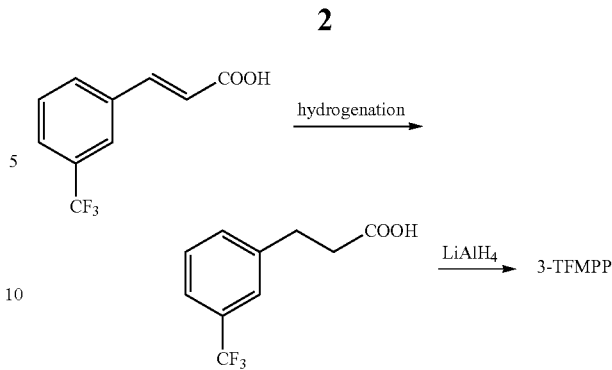

In addition, Y.-Q. Wu, in J. Med. Chem. 2002, 45 (16), 3549-3557 describe the synthesis of 3-(4-trifluoromethylphenyl)propan-1-ol (4-TFMPP) by Wittig reaction of 4-trifluoromethylbenzaldehyde with PPh$_3$CHCOOCH$_3$, subsequent double-bond hydrogenation (H$_2$, Pd/C) and ester reduction with LiAlH$_4$.

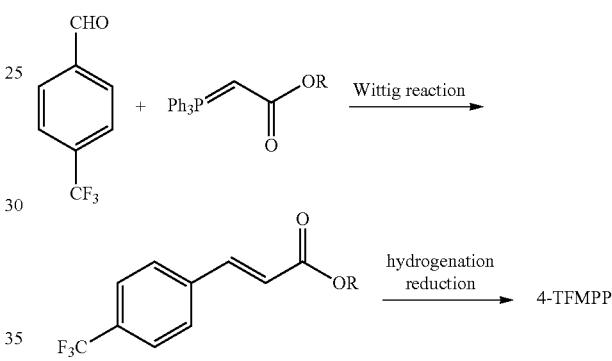

N. J. Green et al., Bioorg. Med. Chem 2003, 11(13), 2991-3014 describe ester condensation of methyl 3-trifluoromethylbenzoate with methyl acetate in the presence of sodium hydride. However, this ester condensation affords a yield of only 78%.

Selective hydrogenation of a β-keto ester to the corresponding saturated esters is described by K. Hattori et al. in Tetrahedron 2001, 57, 4817-4824 or by E. J. McWhorter in J. Org. Chem. 1972, 37(23), 3687-3691 using Pd/C catalysts.

K. Kindler, Arch. Pharm. 1933, 271, 431-439 describe the possibility of reducing the amount of palladium employed in the hydrogenation of a β-keto ester to the corresponding esters by operating in the presence of acidic support material for the catalyst or in the presence of acids or acidic ion exchangers.

Reduction of an ester to the corresponding alcohol in the presence of LiAlH$_4$ is described by Y.-Q. Wu, J. Med. Chem 2002, 45(16), 3549-3557. The same reaction is described by L. A. Saudan et al. Angew. Chem. 2007, 119(39), 7617-74620 using hydrogenation of an ester to the corresponding alcohol in the presence of homogeneous Ru catalysts.

Disadvantages of the processes described here, or substeps of the process of the invention, are the costly use of catalyst during the Heck coupling, and the difficult use of metal hydrides on the industrial scale, which leads to an excessive production of salt and, associated therewith, safety problems and additional costs. In addition, the use of the corresponding aryl halides reduces, owing to their corrosive property, the use of the particular reactor.

The object of the present invention is therefore to provide a process for preparing phenylalkan-1-ols which reduces the use of costly catalysts, and is thus more cost-effective, avoids the use of metal hydrides and aryl halides and nevertheless leads to the desired product in only a few stages.

This object is achieved by a process for preparing phenylalkan-1-ols of the formula I

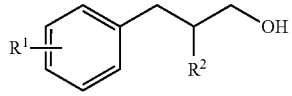

where
R¹ is selected from the group of hydrogen, branched, straight-chain or cyclic alkyl radicals having 1 to 6 C atoms, straight-chain, branched or cyclic alkyl radicals which are substituted by heteroatoms and have 1 to 6 C atoms, substituted or unsubstituted aryl radicals, aryl radicals substituted by heteroatoms, unsubstituted alkoxy radicals, and alkoxy radicals substituted by heteroatoms, and halogen radicals.
R² is selected from the group of hydrogen, branched, straight-chain or cyclic alkyl radicals having 1 to 6 C atoms, substituted or unsubstituted aryl radicals.
where
a) firstly a compound of the formula II

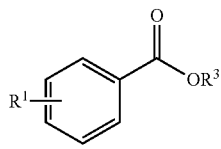

with R³ a branched, straight-chain or cyclic alkyl radical having 1 to 6 C atoms and
R¹ with the above meaning, is reacted with a compound of the formula III

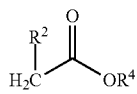

with R⁴ selected from the group of branched, straight-chain or cyclic alkyl radical having 1 to 6 C atoms and
R² with the above meaning
in the presence of alkali metal and/or alkaline earth metal alcoholates and a nonpolar solvent,
b) and the subsequently obtained β-keto ester of the formula IV

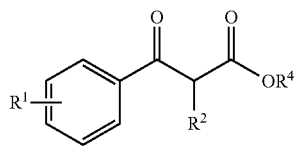

is hydrogenated by selective hydrogenation with palladium as catalyst and in the presence of hydrogen to give the corresponding ester of the formula V

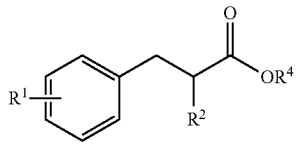

where R¹, R² and R⁴ have the above meaning,
c) and subsequently in the last step the ester of the formula V is hydrogenated by addition of hydrogen and catalyst to the phenylalkan-1-ol of the formula I.

The process of the invention is advantageous when the radical R¹ in the phenyl-alkan-1-ol of the formula I is located in position 3 of the phenyl ring.

The process of the invention is advantageous when R¹ is selected from the group of branched or straight-chain alkyl groups having 1 to 3 C atoms and straight-chain or branched alkyl groups which are substituted by heteroatoms and have 1 to 3 C atoms.

The process of the invention is advantageous when R² corresponds to hydrogen and R¹ corresponds to the trifluoromethyl group.

The process of the invention is advantageous when the nonpolar solvent in stage a) is toluene or xylene or cyclohexane.

The process of the invention is advantageous when the hydrogenation in stage b) is carried out at a temperature in the range from 20 to 150° C. under a pressure of from 1 to 200 bar.

The process of the invention is advantageous when the catalyst employed in stage b) is Pd/C on an acidic support material or in the presence of acids or acidic ion exchangers.

The process of the invention is advantageous when a heterogeneous copper catalyst is employed in stage c).

The process of the invention is advantageous when stage c) is carried out under a pressure in the range from 50 to 350 bar and at a temperature in the range from 100 to 250° C.

The process of the invention is advantageous when the phenylalkan-1-ol of the formula I is obtained after step c) by distillation.

Compounds of the formula II

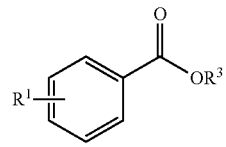

are employed in step a) of the process of the invention. The compounds of the formula II are esters, where the radical R¹ is selected from the group of hydrogen, branched, straight-chain or cyclic alkyl groups having 1 to 6 C atoms, straight-chain or branched alkyl groups which are substituted by heteroatoms and have 1 to 6 C atoms, substituted or unsubstituted aryl radicals, aryl radicals substituted by heteroatoms, unsubstituted alkoxy radicals, and alkoxy radicals substituted by heteroatoms, and halogen radicals. The radical R¹ is particularly preferably selected from the group of hydrogen, methyl, ethyl, n-propyl, i-propyl, n-butyl, sec-butyl, tert-butyl, trifluoromethyl, 1,1,1-trifluoroethyl, methoxy, ethoxy, propyloxy, i-propyloxy, phenyl, tolyl, anisyl, chlorine, bromine, fluorine. $R^1$ is very particularly preferably methyl or trifluoromethyl. In particular, $R^1$ is very particularly preferably trifluoromethyl.

The radical $R^1$ may in principle be located at any position of the aromatic compound. The radical $R^1$ is preferably located in position 3 or 4 relative to the ester function. Very particularly preferably at position 3.

The radical $R^3$ is a branched, straight-chain or cyclic alkyl radical having 1 to 6 C atoms. $R^3$ is preferably selected from the group of methyl, ethyl, n-propyl, i-propyl, n-butyl, sec-butyl, tert-butyl, n-pentyl, cyclopentyl, n-hexyl, cyclohexyl. Methyl and ethyl are preferred. Methyl is very particularly preferred.

The compounds of the formula II are reacted with compounds of the formula III

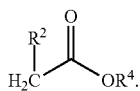

The compounds of the formula III are in this case likewise esters. $R^2$ in this case in the compound of the formula III is selected from the group of hydrogen, branched, straight-chain or cyclic alkyl groups having 1 to 6 C atoms. $R^2$ is particularly preferably from the group of hydrogen, methyl, ethyl, n-propyl, i-propyl, n-butyl, sec-butyl, tert-butyl, n-pentyl, cyclopentyl, n-hexyl, cyclohexyl. $R^2$ is very particularly preferably hydrogen. The reaction of the compound of the formula II with the compounds of the formula III takes place in the presence of alkali metal or alkaline earth metal alcoholates, preferably NaOMe, NaOEt, KOMe, KOEt, KOtBu, particularly preferably KOMe, in a nonpolar solvent. The nonpolar solvent is in this case selected from the group of benzene, toluene, xylene, hexane, cyclohexane, heptane, cycloheptane. Toluene, xylene and cyclohexane are particularly preferred. Toluene and cyclohexane are very particularly preferred The reaction of the compounds of the formula II with the compounds of the formula III takes place at temperatures in the range from 20 to 140° C., preferably in the range from 50 to 80° C.

The β-keto ester of the formula IV subsequently results from the esters of the formula II and III. This β-keto ester of the formula IV is subsequently hydrogenated in step b) selectively to the ester of the formula V. The hydrogenation of step b) takes place in this case in the presence of hydrogen and palladium and of an acid as catalyst. This hydrogenation in step b) is preferably carried out at temperatures in the range from 20 to 150° C., particularly preferably in the range from 20 to 100° C. under a hydrogen pressure in the range from 1 to 200 bar, preferably in the range from 1 to 50 bar. The catalyst used is palladium(0) on a support. Suitable as support are activated carbon, aluminum oxide, silicon oxide, titanium oxide, magnesium oxide, lanthanum oxide, zinc oxide, manganese oxide, zircon oxide, iron oxide, zeolites and clays. The use of activated carbon as support is particularly preferred. The selective hydrogenation particularly preferably proceeds in the presence of an acidic support material for the catalyst or else in the presence of acids or acidic ion exchangers. Acidic support material means support materials which are selected from the group of activated carbon, aluminum oxide, silicon oxide, lanthanum oxide, zeolites and clays and correspondingly have acidic properties. The acids and acidic ion exchangers in whose presence the hydrogenation can take place are selected from the group of hydrochloric acid, sulfuric acid, phosphoric acid, phosphotungstic acid, phosphomolybdic acid, and strongly acidic cation exchangers.

In step c), the ester of the formula V resulting from step b) is subsequently hydrogenated in the presence of hydrogen and of a catalyst to give the corresponding phenylalkan-1-ol of the formula I.

Step c) is preferably carried out at temperatures in the range from 100 to 250° C., particularly preferably in the range from 120 to 200° C. under a pressure in the range from 50 to 350 bar, particularly preferably in the range from 100 to 250 bar.

The catalyst which can be employed is any catalyst which is able both batchwise and continuously to hydrogenate the ester to the alcohol. The catalyst is preferably selected from the group of homogeneous Ru catalysts and heterogeneous copper-containing or nickel-containing catalysts. A catalyst comprising $CuO/Cu/La_2O_3/Al_2O_3$ is particularly preferred.

The phenylalkan-1-ol of the formula I obtained in this way can subsequently be purified by purification processes known to a person skilled in the art. Such purification processes are selected from the group of crystallization, distillation, sublimation, centrifugation and chromatography. Distillation is particularly preferred.

The particularly preferred compound of the phenylalkan-1-ols of the formula I is 3-(3'-trifluoromethylphenyl)propan-1-ol (3-TFMPP).

EXAMPLES

Synthesis of Methyl 3-oxo-3-(3'-trifluoromethylphenyl)propionate

Example 1

920 g (4.20 mol) of ~32% strength KOMe solution are heated to 68° C. Under atmospheric pressure and at an internal temperature of 85-139° C., while 1988 g of iso-xylene are continuously metered in, methanol is distilled out (solvent exchange). When the distillate temperature reaches 138° C., the internal temperature is reduced to 80° C., and 321.6 g (1.56 mol) of methyl 3-trifluoromethylbenzoate are added. Subsequently, 186.0 g (2.51 mol) of methyl acetate are metered in at 78° C. over the course of 3 h. After subsequent stirring at 78° C. for 2 h, a further 321.6 g (4.34 mol) of methyl acetate are metered in over the course of 2 h. After the addition is complete, the mixture is stirred at 78° C. for a further 4 h and then cooled to room temperature. A pH of 7-8 is adjusted by metering in 335 g (3.90 mol) of a 70% strength methanolic solution of acetic acid. The resulting suspension is dissolved by adding 1047 g of water and then the phases are separated. The organic phase is washed with 400 g of sat. NaCl solution, dried over sodium sulfate and concentrated, and the residue (74 g) is analyzed by HPLC.

$C_{benzoate}$=93%
$Y_{keto\ ester}$=88%
$S_{keto\ ester}$=95%

Example 2

1380 g (6.30 mol) of 32% strength KOMe solution are heated to 80° C. Under atmospheric pressure and at an internal temperature of 85-139° C., while 1931 g of iso-xylene are continuously metered in, methanol is distilled out (solvent exchange). When the distillate temperature reaches 138° C., the internal temperature is reduced to 80° C. and 482.4 g (2.36 mol) of methyl 3-trifluoromethylbenzoate are added. Subsequently, 764.2 g (10.31 mol) of methyl acetate are metered in at 80° C. over the course of 6 h. After the addition is complete, the mixture is stirred at 80° C. for a further 6 h and then cooled to room temperature.

A pH of 7-8 is adjusted by metering in 356 g (5.92 mol) of acetic acid. Then 1420 g of water are added, and the phases are separated. The organic phase is concentrated and the residue (562 g) is analyzed by HPLC.

$C_{benzoate}$=97%
$Y_{keto\ ester}$=90%
$S_{keto\ ester}$=93%

Synthesis of Methyl 3-(3'-trifluoromethylphenyl)propionate

Example 3

Use of Pd/C and Amberlyst 15

955 g of methyl 3-oxo-3-(3'-trifluoromethylphenyl)propionate (85% purity) were dissolved in 4800 ml of methanol in a 9 liter autoclave, and 30.0 g of a Pd/C catalyst (5% Pd on carbon, water content 50%) and 24.0 g of the acidic ion exchanger Amberlyst 15 were added. The autoclave was closed and then heated to 60° C., and 10 bar of hydrogen were injected, with the hydrogen being replenished after consumption. After 48 hours, the autoclave was cooled and then decompressed and emptied, resulting in a reaction solution comprising 727 g of methyl 3-(3'-trifluoro-methylphenyl)propionate, equivalent to a yield of 95%.

Example 4

Use of Pd/C and Amberlyst 39

740 g of methyl 3-oxo-3-(3'-trifluoromethylphenyl)propionate (85% purity) were dissolved in 2600 ml of methanol in a 9 liter autoclave, and 18.5 g of a Pd/C catalyst (5% Pd on carbon, water content 50%) and 37.0 g of the acidic ion exchanger Amberlyst 39 were added. The autoclave was closed and then heated to 60° C., and 10 bar of hydrogen were injected, with the hydrogen being replenished after consumption. After 48 hours, the autoclave was cooled and then decompressed and emptied, resulting in a reaction solution comprising 649 g of methyl 3-(3'-trifluoromethylphenyl)propionate, equivalent to a yield of 93%.

Example 5

Use of Pd/C and HCl 20 g of methyl 3-oxo-3-(3'-trifluoromethylphenyl)propionate (85% purity) were dissolved in 100 ml of methanol in a 300 ml autoclave, and 1.0 g of a Pd/C catalyst (5% Pd on carbon, water content 50%) and 0.5 ml of hydrochloric acid (32% strength) were added. The autoclave was closed and then heated to 60° C., and 10 bar of hydrogen were injected, with the hydrogen being replenished after consumption. After 24 hours, the autoclave was cooled and then decompressed and emptied, resulting in a reaction solution comprising 14.3 g of methyl 3-(3'-trifluoromethylphenyl)propionate, equivalent to a yield of 89%.

Example 6

Use of Pd/C 20 g of methyl 3-oxo-3-(3'-trifluoromethylphenyl)propionate (85% purity) were dissolved in 100 ml of methanol in a 300 ml autoclave, and 3.4 g of a Pd/C catalyst (3% Pd on carbon, water content 50%) were added. The autoclave was closed and then heated to 60° C., and 10 bar of hydrogen were injected, with the hydrogen being replenished after consumption. After 24 hours, the autoclave was cooled and then decompressed and emptied, resulting in a reaction solution comprising 14.7 g of methyl 3-(3'-trifluoromethylphenyl)propionate, equivalent to a yield of 92%.

Synthesis of 3-(3'-trifluoromethylphenyl)propan-1-ol (3-TFMPP)

Example 7

20 ml of the product of example 3 (comprising 2.5 g of methyl 3-(3'-trifluoromethylphenyl)propionate) were mixed in a 50 ml autoclave with 2 g of a catalyst of the composition 56% CuO, 15% Cu, 24% $Al_2O_3$ and 4% $La_2O_3$ and stirred at 180° C. under a hydrogen pressure of 200 bar for 24 hours. After cooling and decompression, a solution comprising 2.0 g of 3-TFMPP was discharged, equivalent to a yield of 91%.

Example 8

A solution of methyl 3-(3'-trifluoromethylphenyl)propionate in methanol (content 20% by weight) was passed at 40 g/h under a hydrogen pressure of 200 bar and at 160° C. through a reactor with 100 ml of the catalyst of the composition 56% CuO, 15% Cu, 24% $Al_2O_3$ and 4% $La_2O_3$, metering in hydrogen at 100 Nl/h. The product was found still to contain 0.1% by weight of the precursor in addition to 17.3% by weight of 3-(3'-trifluoromethylphenyl)-1-propanol in the solution, equivalent to a conversion of >99% and an alcohol yield of 98%.

The invention claimed is:

1. A process for preparing a phenylalkan-1-ols of the formula I

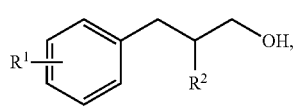

the process comprising:
reacting a compound of the formula II with a compound of the formula III

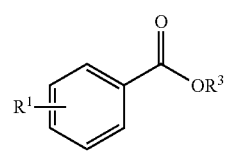

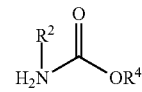

in the presence of alkali metal and/or alkaline earth metal alcoholates, and a nonpolar solvent to obtain a β-keto ester of the formula IV;

hydrogenating the a β-keto ester of the formula IV

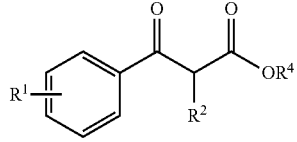

by selective hydrogenation with a palladium catalyst in the presence of hydrogen to produce an ester of the formula V

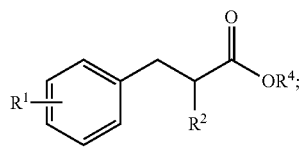

and
hydrogenating the ester of the formula V by addition of a hydrogen and a catalyst and obtaining a phenylalkan-1-ol of formula I,
wherein
$R^1$ is selected from the group consisting of
a hydrogen,
a branched, straight-chain or cyclic alkyl radical having 1 to 6 C atoms,
a straight-chain, branched or cyclic alkyl radical which is substituted by heteroatoms and have 1 to 6 C atoms,
a substituted or unsubstituted aryl radical,
an aryl radical substituted by heteroatoms,
an unsubstituted alkoxy radical,
an alkoxy radical substituted by heteroatoms, and
a halogen radical, $R^2$ is selected from the group consisting of
a hydrogen,
a branched, straight-chain or cyclic alkyl radical having 1 to 6 C atoms, and
a substituted or unsubstituted aryl radical,
$R^3$ is a branched, straight-chain or cyclic alkyl radical having 1 to 6 C atoms, and
$R^4$ is a branched, straight-chain or cyclic alkyl radical having 1 to 6 C atoms.

2. The process according to claim 1, wherein $R^1$ is located in position 3 in the phenylalkan-1-ol of the formula I.

3. The process according to claim 1, wherein $R^1$ is selected from the group consisting of
a branched or straight-chain alkyl group having 1 to 3 C atoms and
a branched or straight-chain alkyl group substituted by heteroatoms having 1 to 3 C atoms.

4. The process according to claim 1, wherein $R^2$ is a hydrogen and $R^1$ is a trifluoromethyl group.

5. The process according to claim 1, wherein the nonpolar solvent is toluene or xylene or cyclohexane.

6. The process according to claim 1, wherein the hydrogenation of the β-keto ester of the formula IV is carried out at a temperature in the range from 20 to 150° C. under a pressure of from 1 to 200 bar.

7. The process according to claim 1, wherein the palladium catalyst is Pd/C on an acidic support material or in the presence of acids or acidic ion exchangers.

8. The process according to claim 1, wherein a heterogeneous copper catalyst is employed in the hydrogenation of the ester of the formula V.

9. The process according to claim 1, wherein the hydrogenation of the ester of the formula V is carried out under a pressure in the range from 100 to 350 bar and at a temperature in the range from 100 to 350° C.

10. The process according to claim 1, wherein the phenylalkan-1-ol of the formula I is obtained by distillation after the hydrogenation of the ester of the formula V.

* * * * *